United States Patent [19]

Hill et al.

[11] 3,975,537

[45] Aug. 17, 1976

[54] PHARMACEUTICAL COMPOSITIONS AND METHODS OF PRODUCING CORONARY VASODILATION

[75] Inventors: David T. Hill, North Wales; Bernard Loev, Broomall, both of Pa.

[73] Assignee: Smith Kline, Philadelphia, Pa.

[22] Filed: Feb. 20, 1975

[21] Appl. No.: 551,581

Related U.S. Application Data

[63] Continuation-in-part of Ser. No. 399,573, Sept. 21, 1973, Pat. No. 3,880,891.

[52] U.S. Cl. ................................. 424/285; 424/248; 424/267; 424/274
[51] Int. Cl.² ................. A61K 31/34; A61K 31/40; A61K 51/445; A61K 31/535
[58] Field of Search ........... 424/248, 267, 274, 285

[56] References Cited
UNITED STATES PATENTS 3,248,401  4/1966  Tondeur et al. ............. 260/346.2

OTHER PUBLICATIONS

Derwent 719545-B, Abstracting Belgium 766392 Q 10-28-71.

Derwent 81178T-B, Abstracting Belgium 784260 Q 12-1-72.

Derwent 21007v/12, Abstracting Belgium 804550 (6-3-74).

*Primary Examiner*—Stanley J. Friedman
*Attorney, Agent, or Firm*—Janice E. Williams; Joan S. Keps; William H. Edgerton

[57] ABSTRACT

Pharmaceutical compositions and methods of producing coronary vasodilation by administering substituted benzofurans, for example 2-n-butyl-3-[4′-(2-hydroxy-3-isopropylamino)propoxybenzoyl]benzofuran.

17 Claims, No Drawings

PHARMACEUTICAL COMPOSITIONS AND METHODS OF PRODUCING CORONARY VASODILATION

This application is a continuation-in-part of application Ser. No. 399,573, filed Sept. 21, 1973, now U.S. Pat. No. 3,880,891.

This invention relates to new substituted benzofurans which have useful pharmacological activity. More specifically, the compounds of this invention have coronary vasodilator activity and are useful in the treatment of angina pectoris. In addition, these compounds may be useful as hypotensive agents.

The compounds of this invention are represented by the following structural formula:

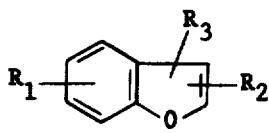

FORMULA I or a pharmaceutically acceptable acid addition salt thereof, in which:

$R_1$ is hydrogen, halogen, lower alkyl, lower alkoxy or trifluoromethyl;

$R_2$ is hydrogen, lower alkyl or phenyl$(CH_2)_n$ where $n$ is 0 or 1 and the phenyl moiety is optionally substituted with lower alkyl, lower alkoxy, trifluoromethyl, halogen, $NH_2$, NH(lower alkyl) or N(lower alkyl)$_2$;

$R_3$ is

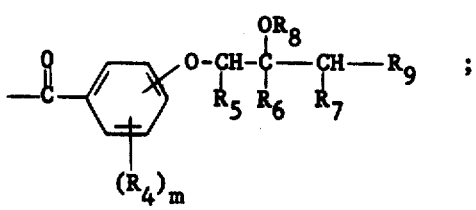

$R_4$ is hydrogen, halogen, lower alkyl or lower alkoxy;

$m$ is 1 or 2;

$R_5$, $R_6$ and $R_7$ are hydrogen or one of $R_5$, $R_6$ and $R_7$ is methyl or ethyl;

$R_8$ is hydrogen or lower alkanoyl; and $R_9$ is NH(lower alkyl), N(lower alkyl)$_2$, NH(benzyl), N(lower alkanoyl)(lower alkyl), piperidino, pyrrolidino, morpholino or succinimido.

As used herein, the terms lower alkyl and lower alkoxy denote groups having from one to four carbon atoms and lower alkanoyl denotes groups having from two to four carbon atoms.

Preferred compounds of this invention are represented by Formula I in which $R_2$ is hydrogen, lower alkyl or phenyl$(CH_2)_n$ where $n$ is 0 or 1 and the phenyl moiety is optionally substituted with methyl, methoxy, trifluoromethyl or chloro, $R_5$, $R_7$ and $R_8$ are hydrogen, $R_6$ is hydrogen or methyl and $R_9$ is NH(isopropyl) or NH(t-butyl). Most preferred are those compounds in which $R_1$ is hydrogen or chloro in the 5-position, $R_2$ is hydrogen, lower alkyl or phenyl$(CH_2)_n$ where $n$ is 0 or 1 and the phenyl moiety is optionally substituted with methyl, methoxy, trifluoromethyl or chloro, $R_4$ is hydrogen or halogen, $m$ is 1, $R_5$, $R_6$, $R_7$ and $R_8$ are hydrogen and $R_9$ is NH(isopropyl) or NH(t-butyl).

Advantageous compounds of this invention are represented by Formula I in which $R_1$ is hydrogen, $R_2$ is hydrogen, lower alkyl or phenyl$(CH_2)_n$ where $n$ is 0 or 1 and the phenyl moiety is optionally substituted with methyl, methoxy, trifluoromethyl or chloro, $R_3$ is

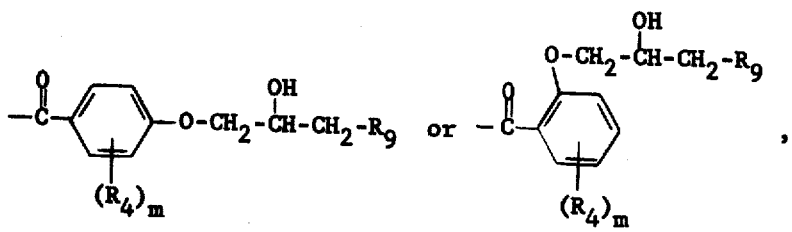

$R_4$ is hydrogen or chloro, $m$ is 1 and $R_9$ is NH(isopropyl) or NH(t-butyl).

Particularly preferred are the compounds 2-n-butyl-3-[4'-(2-hydroxy-3-isopropylamino)propoxybenzoyl]-benzofuran, 2-n-butyl-3-[3'-chloro-4'-(2-hydroxy-3-isopropylamino)propoxybenzoyl]benzofuran, 2-n-butyl-3-[4'-chloro-2'-(2-hydroxy-3-isopropylamino)-propoxybenzoyl]benzofuran and 2-(4'-chlorobenzyl)-3-[4'-(2-hydroxy-3-isopropylamino)-propoxybenzoyl]-benzofuran.

The compounds of this invention may exist as optical isomers due to the asymmetric carbon atom in the side chain of the acyl group. All of the isomers, including separated isomers and mixtures thereof, are included within the scope of this invention.

The compounds of Formula I in which $R_8$ is hydrogen and $R_9$ is NH(lower alkyl), N(lower alkyl)$_2$, NH(benzyl), piperidino, pyrrolidino, morpholino or succinimide are prepared as shown in the following scheme:

SCHEME I

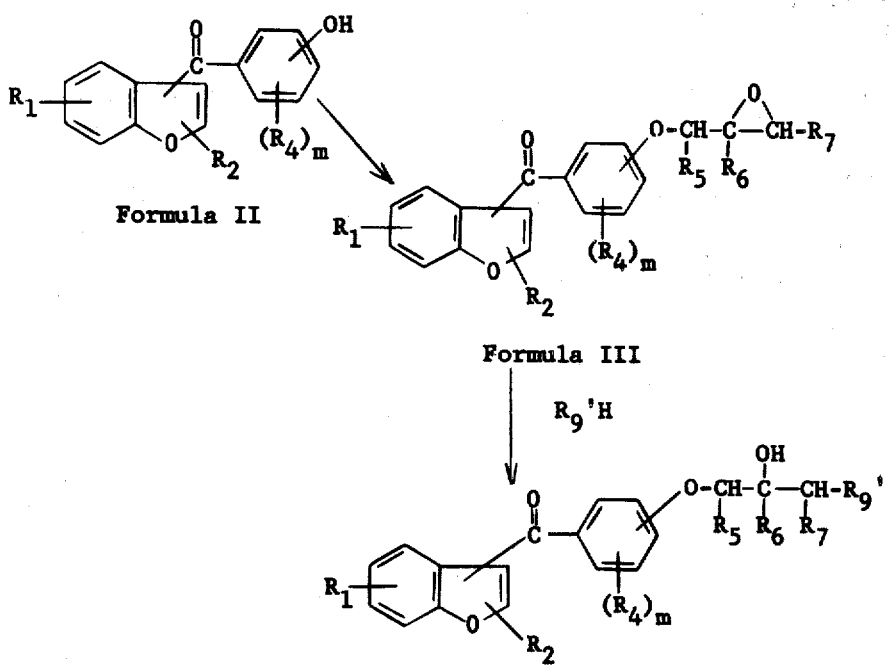

The terms $R_1$, $R_2$, $R_4$, $R_5$, $R_6$, $R_7$ and $m$ are defined as above and $R_9'$ is NH(lower alkyl), N(lower alkyl)$_2$, NH(benzyl), piperidino, pyrrolidino, morpholino or succinimido.

According to the above procedure, a hydroxyphenyl benzofuranyl ketone of Formula II is converted to the epoxy intermediate III which is then opened by reaction with an appropriate amine ($R_9'H$). When $R_5$, $R_6$ and $R_7$ are hydrogen, the epoxy intermediates of Formula III are prepared by reaction of a compound of Formula II with an epihalohydrin such as epichlorohydrin or epibromohydrin in the presence of a base such as sodium hydroxide or potassium carbonate in a solvent such as water, ethanol or acetone. When one of $R_5$, $R_6$ and $R_7$ is methyl or ethyl, the corresponding compounds of Formula III are prepared by reaction of a hydroxyphenyl benzofuranyl ketone with a chloroalkene to give an alkenyloxyphenyl benzofuranyl ketone which is then epoxidized with m-chloroperbenzoic acid.

The ring opening of the epoxy intermediates of Formula III is preferably carried out in a minimum amount of a solvent such as ethanol or with excess amine as solvent in a Parr pressure bomb at from about 25° to about 150°C. for from one to about 48 hours.

The product propanolamines are isolated and purified as such by standard techniques including solvent extraction, crystallization and chromatographic methods or as the corresponding acid addition salts which are formed with organic and inorganic acids according to methods known to the art. Thus, a solution of the amine in ether or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether or chloroform, with the desired salt separating directly. Exemplary of such organic salts are those with maleic, fumaric, benzoic, ascorbic, pamoic, succinic, hexamic, oxalic, bismethylenesalicyclic, methanesulfonic, ethanedisulfonic, acetic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

Also formed in the reaction of II with epichlorohydrin is a compound of Formula IV:

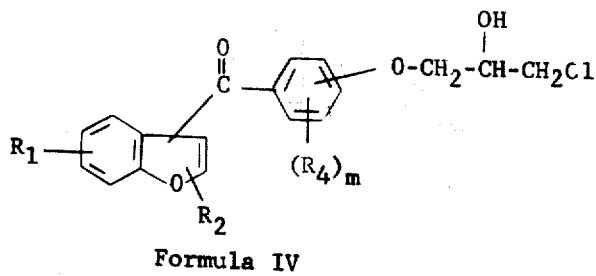

Formula IV

The ratio of III and IV is variable and depends on the nature of $R_1$, $R_2$ and $R_4$, $m$, their relative positions and the base employed in the reaction. III and IV are separated by standard wet or dry column chromatographic methods. The compounds of Formula IV may be converted to the corresponding epoxy intermediates of Formula III by stirring a solution of IV in aqueous dioxane containing a base such as sodium hydroxide for from one to about 12 hours at about 25° to about 100°C.; or may be reacted with an amine as previously described to give the corresponding compounds of Formula I directly.

The hydroxyphenyl benzofuranyl ketone starting materials of Scheme I, in which $R_2$ is in the 2-position and $R_3$ is in the 3-position of the benzofuran nucleus (V) are either known to the art or are prepared as outlined below:

pyridine hydrochloride or boron tribromide. These and other methods are described by Buu-hoi et al., J. Chem. Soc. 3693 (1955), 625 (1957), 2593 (1957), 173 (1964) and in Japanese Patent 2482/64.

Alternatively, the hydroxyphenyl benzofuranyl ketone starting materials are prepared by addition of a methoxyphenyl magnesium halide to a 3-cyanobenzofuran followed by hydrolysis and subsequent demethylation as previously described.

The benzofuran nuclei used as starting materials in Scheme Ii are either known to the art or are prepared by one of the general methods for the synthesis of benzofurans described by Buu-Hoi et al., supra, Tanaka, J. Amer. Chem. Soc. 73:872 (1951), Bisagni et al., J. Chem. Soc. 3688 (1955), Grinev et al., Zhur. Obshchei Khim. 27:1087 (1957) and Castro et al., J. Org. Chem. 28:3313 (1963), 31:4071(1966), in Rodd, Chemistry

SCHEME II

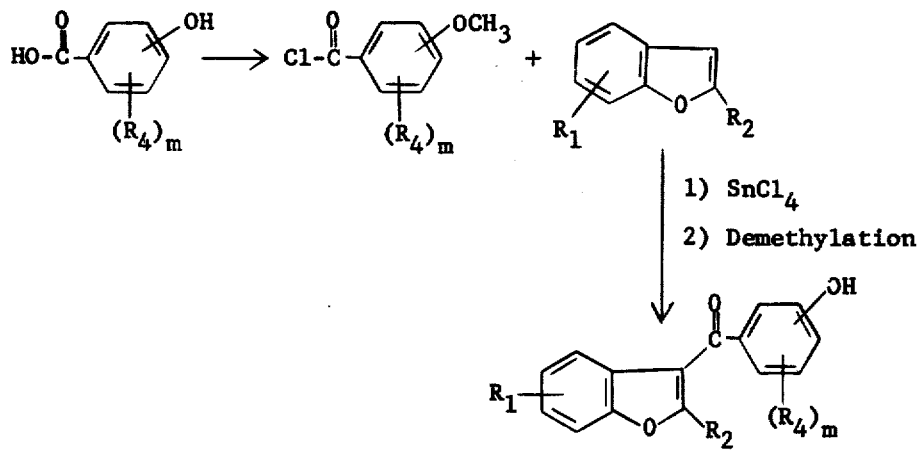

Formula V

According to Scheme II, a hydroxybenzoic acid is methylated by standard methods, for example with dimethyl sulfate, converted to the corresponding acid chloride with thionyl chloride and subsequently used to acylate a benzofuran nucleus by standard procedures, for example in the presence of stannic chloride in a solvent such as methylene chloride or carbon disulfide. The methoxyphenyl benzofuranyl ketones are demethylated by known methods, for example by use of of Carbon Compounds Vol. IV-A, 168–191 and in French Patent 1,537,206.

To prepare the compounds of Formula I in which $R_2$ is in the 3-position and $R_3$ is in the 2-position of the benzofuran nucleus, the required hydroxyphenyl benzofuranyl ketone starting materials of Scheme I are either known to the art or are prepared by the method of Buu-Hoi et al., J. Chem. Soc. 3693 (1955) and 2593 (1957) shown in Scheme III:

SCHEME III

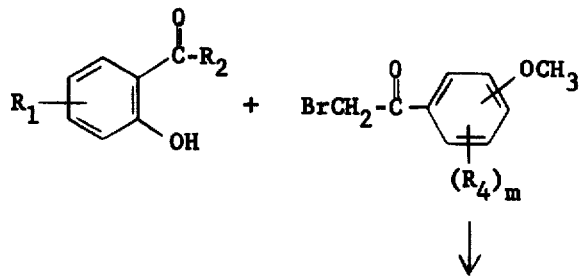

SCHEME III -continued

1) Base
2) Demethylation

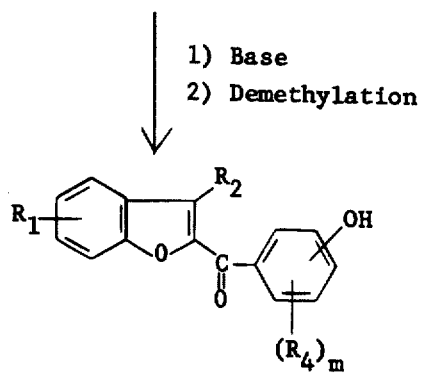

Formula VI

Reaction of a salicylic acid or an o-hydroxyphenyl ketone with a substituted α-bromoacetophenone in the presence of base followed by demethylation as described above gives the hydroxyphenyl benzofuranyl ketones of Formula VI.

The compounds of Formula I in which $R_4$ is bromine, $m$ is 2, $R_8$ is hydrogen and $R_9$ is $R_9'$ as defined above may also be prepared by treatment of the corresponding hydroxyphenyl benzofuranyl ketones where $R_4$ is hydrogen with bromine in acetic acid followed by epoxide formation and subsequent ring opening with $R_9'H$. Similarly, treatment of the hydroxyphenyl benzofuranyl ketones where $R_4$ is hydrogen with N-bromosuccinimide in dimethylformamide gives the compounds of Formula II where $R_4$ is bromo and $m$ is 1. When $R_4$ is chloro and $m$ is 2, the compounds of Formula II may be alternatively prepared from reaction of the hydroxyphenyl benzofuranyl ketones where $R_4$ is hydrogen with potassium hypochlorite in methanol and aqueous base.

The compounds of this invention in which $R_8$ is lower alkanoyl and $R_9$ is N(lower alkanoyl)(lower alkyl) are prepared from the corresponding compounds of Formula I where $R_8$ is hydrogen and $R_9$ is NH(lower alkyl) by conventional methods, for example, by reaction of the hydroxy compound with a lower alkanoic acid anhydride or a lower alkanoyl halide. Also formed in this reaction are the corresponding compounds of Formula I in which $R_8$ is lower alkanoyl and $R_9$ is NH(lower alkyl). These products are separated by standard chromatographic methods. When $R_8$ is hydrogen and $R_9$ is N(lower alkyl)$_2$, piperidino, pyrrolidino, morpholino or succinimido, treatment with a lower alkanoic acid anhydride or a lower alkanoyl halide yields the corresponding compounds of Formula I in which $R_8$ is lower alkanoyl. Basic hydrolysis of the N,O-di-(lower alkanoyl) compounds of this invention give the corresponding compounds of Formula I in which $R_8$ is hydrogen and $R_9$ is N(lower alkanoyl)(lower alkyl).

The coronary vasodilator activity and hypotensive effects of the compounds represented by Formula I are demonstrated in dogs by an increase in coronary blood flow with concomitant decrease of mean arterial blood pressure upon intravenous administration of doses of from about 0.5 to about 5.0 mg./kg. These parameters are measured as follows:

Adult mongrel dogs (13–16 kg.) are pretreated with 2 mg./kg. s.c. of morphine sulfate followed in one hour by intravenous administration of 1–1.5 ml./kg. of an aqueous solution containing 1.5% chloralose and 20% urethane. Supplemental doses of morphine and chloralose-urethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic Flowmeter and Flo-Probe (MDS).

In addition, many of the compounds of this invention, for example those represented by Formula I in which $R_1$ is hydrogen, $R_3$ is

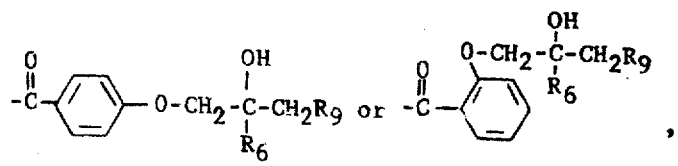

$R_6$ is hydrogen or methyl and $R_9$ is NH(lower alkyl), N(lower alkyl)$_2$ or NH(benzyl) also inhibit or attenuate the chronotropic effect of isoproterenol-induced tachycardia upon administration to dogs at doses of from about 0.63 to about 5.0 mg./kg. i.v. Abad et al. [Acta Pharmacol. et Toxicol. 25:85 (1967)] have correlated the inhibition of isoproterenol-induced tachycardia to utility as an antianginal agent.

Pharmaceutical compositions having coronary vasodilator activity, in dosage unit form, comprising a pharmaceutical carrier and, in an amount sufficient to produce coronary vasodilation, a compound of Formula I or a pharmaceutically acceptable acid addition salt thereof, and methods of producing coronary vasodilation by administering these compounds are also objects of this invention.

The pharmacologically active compounds of this invention may be administered orally or parenterally in an amount to produce the desired activity.

Preferably, the compounds are administered in conventional dosage unit forms prepared by combining an appropriate dose of the compound with standard pharmaceutical carriers. The dosage units will contain the active medicament in an amount of from about 100 mg. to about 600 mg., preferably 150 mg. to 300 mg., per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical compositions are prepared by conventional techniques involving procedures such as mixing, granulating and compressing or variously mixing and dissolving the ingredients as appropriate to the desired composition.

The method of producing coronary vasodilator activity in accordance with this invention comprises administering internally to an animal an effective amount of a compound of Formula I or a pharmaceutically acceptable acid addition salt thereof. The compound will preferably be administered in a dosage unit form as described above orally or parenterally, the oral route being preferred. Advantageously, equal doses will be administered one to two times daily with the daily dosage regimen being from about 200 mg. to about 1200 mg., preferably from about 300 mg. to about 600 mg., of the active medicament. When the method described above is carried out, coronary vasodilation is produced.

One skilled in the art will recognize that in determining the amounts of the active medicament in the claimed compositions and used in the claimed methods, the activity of the particular medicament as well as the size of the host animal must be considered.

The following examples illustrate the invention but are not to be construed as limiting the scope thereof. Temperatures are in degrees Centigrade unless otherwise stated.

When formed, acid addition salts may be converted to the corresponding free amines by treating a solution of the salt in water, a chloroform-water or a benzene-water mixture with 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through an Amberlite IRA-401 chloride ion exchange column.

EXAMPLE 1

2-n-Butyl-3-[4'-(2-hydroxy-3-isopropylamino)propoxybenzoyl]benzofuran

To a solution of 8.7 g. (0.03 mol.) of 2-n-butyl-3-(4'-hydroxybenzoyl)benzofuran in 100 ml. of water containing 1.4 g. (0.035 mol.) of sodium hydroxide was added dropwise 4.0 g. (0.044 mol.) of epichlorohydrin. The reaction mixture was stirred and refluxed for one hour, then cooled and extracted with chloroform. The extracts were washed with water and a saturated aqueous solution of sodium chloride, dried ($MgSO_4$) and concentrated to yield a mixture of 2-n-butyl-3-[4'-(2,3-epoxy)propoxybenzoyl]benzofuran and 2-n-butyl-3-[4'-(2-hydroxy-3-chloro)propoxybenzoyl]benzofuran which was separated by dry column chromatography on alumina with chloroform as the eluant.

The chlorohydrin product was dissolved in 10% aqueous dioxane containing an excess of one molar equivalent of sodium hydroxide and stirred at 25° for 2 hours to effect conversion to the epoxide, m.p. 61°–62°.

A solution of 1.5 g. (0.004 mol.) of 2-n-butyl-3-[4'-(2,3-epoxy)propoxybenzoyl]benzofuran and 25 ml. of isopropylamine in 20 ml. of ethanol was heated in a Parr pressure bomb for 12 hours at 120°. After cooling, the solvent and excess amine were removed in vacuo to give the title compound which was dissolved in ether and treated with an ethereal solution of hydrogen chloride until pH 2–4. The precipitated salt was collected and recrystallized from isopropanol-isopropyl ether to give the title compond as its hydrochloric acid salt, m.p. 123°–125°.

The salt is dissolved in a minimum amount of water to which chloroform is added. While stirring, 10% aqueous sodium carbonate is added until the solution becomes distinctly basic (pH 9–11). The layers are separated, the aqueous phase is extracted repeatedly with chloroform and the combined extracts are washed with water, dried ($MgSO_4$) and concentrated to give the title compound.

The title compound is also prepared by heating a solution of 2-n-butyl-3-[4'-(2-hydroxy-3-chloro)-propoxybenzoyl]benzofuran (chlorohydrin product) in ethanol with isopropylamine as described above.

EXAMPLE 2

2-n-Butyl-3-[3',5'-diiodo-4'-(2-hydroxy-3-t-butylamino)-propoxybenzoyl]benzofuran A mixture of 10.8 g. (0.02 mol.) of 2-n-butyl-3-(3',-5'-diiodo-4'-hydroxybenzoyl)benzofuran, 1 g. (0.025 mol.) of sodium hydroxide and 3 g. of epichlorohydrin in 100 ml. of water was stirred at 25° for 12 hours. The reaction mixture was extracted with chloroform and the extracts were washed with water, dried ($MgSO_4$)

and concentrated to give a mixture of 2-n-butyl-3-[3',-5'-diiodo-4'-(2,3-epoxy)propoxybenzoyl]benzofuran and 2-n-butyl-3-[3',5'-diiodo-4'-(2-hydroxy-3-chloro)-propoxybenzoyl]benzofuran which was separated by dry column chromatography on alumina with methylene chloride.

A solution of 1 g. (0.0017 mol.) of 2-n-butyl-3-[3',5'-diiodo-4'-(2,3-epoxy)propoxybenzoyl]benzofuran and 10 ml. of t-butylamine in 50 ml. of ethanol was stirred at 25° for 24 hours. The solvent and excess amine were removed in vacuo to give the title compound which was converted to its hydrochloric acid salt as described in Example 1.

EXAMPLE 3

2-n-Butyl-3-[4'-(2-hydroxy-3-piperidino)propoxybenzoyl]-benzofuran

A solution of 2-n-butyl-3-[4'-(2,3-epoxy)propoxybenzoyl] benzofuran and excess piperidine in ethanol was refluxed for 12 hours. Concentration in vacuo gave the title compound which was dissolved in ethanol and converted to its hydrochloric acid salt by the procedure described in Example 1, m.p. 131°–133° (ethanol-ether).

EXAMPLE 4

When pyrrolidine, morpholine or 30% aqueous methyl amine was substituted in the procedure of Example 3 for piperidine, there was obtained 2-n-butyl-3-[4'-(2-hydroxy-3-pyrrolidino)propoxybenzoyl]benzofuran, 2-n-butyl-3-[4'-(2-hydroxy-3-morpholino)-propoxybenzoyl]benzofuran and 2-n-butyl-3-[4'-(2-hydroxy-3-methylamino)propoxybenzoyl]-benzofuran, respectively, The substituted benzofurans prepared above were converted to their hexamic acid salts by addition of a 10% solution of hexamic acid in ethanol to a solution of the amine in ethanol.

EXAMPLE 5

2-n-Butyl-3-[4'-(2-hydroxy-3-t-butylamino)propoxybenzoyl]-benzofuran

The title compound was prepared by substitution of t-butylamine in the procedure of Example 3 for piperidine. The corresponding hydrochloric acid salt was prepared as described in Example 1, m.p. 122°–123° (ethanol).

EXAMPLE 6

2-n-Butyl-3-[4'-(2-hydroxy-3-succinimido)propoxybenzoyl]-benzofuran

A mixture of 8.0 g. (0.024 mol.) of 2-n-butyl-3-[4'-(2,3-epoxy)propoxybenzoyl]benzofuran and 2.5 g. (0.025 mol.) of succinimide in 100 ml. of ethanol containing 1 ml. of pyridine was refluxed with stirring for 22 hours. The reaction mixture was cooled to ambient temperature, then refrigerated for 12 hours. The precipitate was collected by filtration, washed with ethanol and ether and dried to give the title compound, m.p. 127°–130° (ethanol).

EXAMPLE 7

2-n-Butyl-3-[3',5'-dibromo-4'-(2-hydroxy-3-isopropylamino)-propoxybenzoyl]benzofuran To a solution of 15 g. (0.051 mol.) of 2-n-butyl-3-(4'-hydroxybenzoyl)benzofuran in 150 ml. of 1:1 acetic acid-water was added dropwise a solution of 8.5 g. of bromine in 20 ml. of acetic acid. The reaction mixture was stirred at 25° for three hours, then it was filtered and the solid product was washed with water, aqueous sodium bisulfite, 5% aqueous sodium bicarbonate and again with water. The crude product was chromatographed on alumina with 2:1 chloroform-methanol as eluant to give 2-n-butyl-3-(3',5'-dibromo-4'-hydroxybenzoyl)benzofuran.

A mixture of 7 g. (0.014 mol.) of 2-n-butyl-3-(3',5'-dibromo-4'-hydroxybenzoyl)benzofuran, 1g. (0.025 mol.) of sodium hydroxide and 15 ml. of epichlorohydrin in 100 ml. of water was refluxed for one hour. After cooling, chloroform was added to the reaction mixture and the layers were separated. The organic phase was washed with water, dried ($Na_2SO_4$) and concentrated to give a mixture of 2-n-butyl-3-[3',5'-dibromo-4'-(2,3-epoxy)propoxybenzoyl]benzofuran and 2-n-butyl-3-[3',5'-dibromo-4'-(2-hydroxy-3-chloro)propoxybenzoyl]benzofuran. The mixture was separated by dry column chromatography on alumina with chloroform as eluant and the chlorohydrin was converted to additional epoxy compound as described in Example 1.

2-n-Butyl-3-[3',5'-dibromo-4'-(2,3-epoxy)propoxybenzoyl]benzofuran (3.0 g., 0.006 mol.) was heated with 25 ml. of isopropylamine in a Parr bomb at 80° for two hours. After cooling, the reaction mixture was concentrated in vacuo and the residue was chromatographed on alumina with chloroform as eluant to give the title compound, m.p. 112°–113° (ether).

EXAMPLE 8

2-n-Butyl-3-[3'-bromo-4'-(2-hydroxy-3-isopropylamino)propoxybenzoyl]benzofuran

A mixture of 10.0 g. (0.034 mol.) of 2-n-butyl-3-(4'-hydroxybenzoyl)benzofuran and 6.1 g. (0.034 mol.) of N-bromosuccinimide in 150 ml. of damp dimethylformamide was refluxed for 12 hours. The reaction mixture was poured into water and extracted with chloroform. The extracts were washed repeatedly with water, then dried ($Na_2SO_4$) and concentrated to give 2-n-butyl-3-(3'-bromo-4'-hydroxybenzoyl)-benzofuran.

2-n-Butyl-3-(3'-bromo-4'-hydroxybenzoyl)benzofuran was converted to 2-n-butyl-3-[3'-bromo-4'-(2,3-epoxy)propoxybenzoyl]benzofuran by treatment with epichlorohydrin as described in the procedure of Example 7.

The epoxide (4 g., 0.009 mol.) was heated with 20 ml. of isopropylamine at 80° for 2.5 hours as described in Examples 1 and 7 to give the title compound.

EXAMPLE 9

2-n-Butyl-3-[3'-methyl-4'-(2-hydroxy-3-isopropylamino)propoxybenzoyl]benzofuran

A solution of 11.5 g. (0.07 mol.) of 3-methyl-4-methoxybenzoic acid and 10.7 g. (0.09 mol.) of thionyl chloride in 60 ml. of methylene chloride was refluxed on a steam bath for two hours. Concentration in vacuo and distillation of the residue gave 3-methyl-4-methoxybenzoic acid chloride, m.p. 37°–39°.

To a cooled, stirred solution of 10.8 g. (0.058 mol.) of 3-methyl-4-methoxybenzoic acid chloride and 9.4 g. (0.054 mol.) of 2-n-butylbenzofuran in 40 ml. of carbon disulfide was added dropwise over a 20 minute interval 28.2 g. (0.108 mol.) of stannic chloride. After addition, the reaction mixture was warmed to ambient temperature and stirred for two hours. The mixture was then poured onto 100 ml. of ice-water and stirred for one hour. The solvent was removed, the product extracted into chloroform and the extracts were washed with water, dried ($Na_2SO_4$) and concentrated in vacuo to give 2-n-butyl-3-(3'-methyl-4'-methoxybenzoyl)-benzofuran.

2-n-Butyl-3-(3'-methyl-4'-methoxybenzoyl)benzofuran (17.5 g., 0.05 mol.) was combined with 50 g. of freshly distilled pyridine hydrochloride and the mixture was refluxed one hour. The hot mixture was poured with stirring onto an ice-dilute hydrochloric acid mixture and the precipitate was collected to give 2-n-butyl-3-(3'-methyl-4'-hydroxybenzoyl)benzofuran.

2-n-Butyl-3-[3'-methyl-4'-(2,3-epoxy)propoxybenzoyl]benzofuran was prepared from 2-n-butyl-3-(3'-methyl-4'-hydroxybenzoyl)benzofuran and epichlorohydrin as described in Example 7.

Opening of the epoxy compound with isopropylamine to give the title compound was accomplished as described in Example 7.

EXAMPLE 10

2-n-Butyl-3-[3',5'-dimethyl-4'-(2-hydroxy-3-isopropylamino)-propoxybenzoyl]benzofuran To a cooled (ice bath) mixture of 9.4 g. (0.054 mol.) of 2-n-butylbenzofuran and 11.5 g. (0.058 mol.) of 3,5-dimethyl-4-methoxybenzoic acid chloride in 100 ml. of methylene chloride was added dropwise 28.7 g. (0.11 mol.) of stannic chloride. The reaction mixture was allowed to warm to ambient temperature, then stirred for 2 hours. Water was slowly added to the mixture and it was stirred an additional 30 minutes. The layers were separated and the organic phase was washed with water until the washings were neutral, dried ($MgSO_4$) and concentrated to give 2-n-butyl-3-(3',5'-dimethyl-4'-methoxybenzoyl)benzofuran.
2-n-Butyl-3-(3',5'-dimethyl-4'-methoxybenzoyl)-benzofuran was demethylated with pyridine hydrochloride as previously described to give 2-n-butyl-3-(3',5'-dimethyl-4'-hydroxybenzoyl)benzofuran which was treated with epichlorohydrin followed by isopropylamine as described in the procedure of Example 7 to ultimately give the title compound.

2-n-Butyl-3-[3',5'-dimethyl-4'-(2-hydroxy-3-isopropylamino)propoxybenzoyl]benzofuran was converted to the corresponding hydrochloric acid salt as described in Example 1, m.p. 202°–203° (ethanol-ether).

EXAMPLE 11

2-n-Butyl-3-[3'-chloro-4'-(2-hydroxy-3-isopropylamino)propoxybenzoyl]benzofuran

A solution of 25 g. (0.14 mol.) of 3-chloro-4-hydroxybenzoic acid in 200 ml. of methanol containing 2 ml. of sulfuric acid was refluxed for 12 hours. After cooling, excess methanol was evaporated, water was added to the residue and it was made basic with 10% aqueous sodium hydroxide. The precipitate was collected, washed with water and dried in vacuo to give 3-chloro-4-hydroxybenzoic acid methyl ester, m.p. 105°–107°C.

To a cooled solution of 14.5 g. (0.078 mol.) of 3-chloro-4-hydroxybenzoic acid methyl ester and 4.0 g. (0.1 mol.) of sodium hydroxide in 100 ml. of water was dropwise added 9.8 g. (7.3 ml., 0.079 mol.) of dimethyl sulfate. The reaction mixture was refluxed for two hours. After cooling, ether was added and the layers were separated. The organic phase was washed with water, dilute sulfuric acid and water, dried ($Na_2SO_4$) and concentrated in vacuo to give 3-chloro-4-methoxybenzoic acid methyl ester, m.p. 72°–74°.

A mixture of 10.4 g. (0.052 mol.) of 3-chloro-4-methoxybenzoic acid methyl ester and 3.5 g. (0.09 mol.) of sodium hydroxide in 150 ml. of water was refluxed for two hours. The reaction mixture was cooled and acidified with 10% aqueous hydrochloric acid to precipitate 3-chloro-4-methoxybenzoic acid, m.p. 199°–202°. The acid was refluxed with thionyl chloride as described in the procedure of Example 9 to give 3-chloro-4-methoxybenzoic acid chloride, m.p. 55°–57°.

2-n-Butyl-3-(3'-chloro-4'-methoxybezoyl)benzofuran was prepared by acylation of 2-n-butylbenzofuran with 3-chloro-4-methoxybenzoic acid chloride as described in the procedure of Example 10. The subsequent steps of demethylation, epoxide formation and ring opening of the 2-n-butyl-3-[3'-chloro-4'-(2,3-epoxy)propoxybenzoyl]benzofuran to give the title compound were accomplished as previously described.

Addition of an ethereal solution of oxalic acid to a solution of the title compound in ether gave the oxalic acid addition salt. The oxalate was converted to the hydrochloric acid salt by passage of a solution of 2-n-butyl-3-[3'-chloro-4'-(2-hydroxy-3-isopropylamino)-propoxybenzoyl]benzofuran oxalate in ethanol through an Amberlite IRA-401 chloride ion exchange column.

EXAMPLE 12

2-n-Butyl-3-[3',5'-dichloro-4'-(2-hydroxy-3-isopropylamino)propoxybenzoyl]benzofuran To a suspension of 56.6 g. of calcium hypochlorite in 225 ml. of warm water was added a solution of 39.6 g. of potassium carbonate and 11.3 g. of potassium hydroxide in 120 ml. of water. The reaction vessel was stoppered and vigorously shaken until the gel which initially formed became fluid. The solid material was removed by filtration and the filtrate of aqueous potassium hypochlorite (45.3 g., 0.35 mol.) was then added dropwise to a cooled (ice bath), stirred solution of 38.3 g. (0.13 mol.) of 2-n-butyl-3-(4'-hydroxybenzoyl)benzofuran in 200 ml. of methanol and 100 ml. of 5% aqueous sodium hydroxide. After addition the reaction mixture was refluxed for five minutes, then cooled and left to stand at 25° for 12 hours. The mixture was acidified by addition of an ethereal solution of hydrogen chloride, additional amounts of ether were added and the layers were separated. The organic phase was washed with water, dried (Na₂SO₄) and concentrated in vacuo to yield 2-n-butyl-3-(3',5'-dichloro-4'-hydroxybenzoyl)benzofuran, m.p. 110°-114° (cyclohexane).

2-n-Butyl-3-(3',5'-dichloro-4'-hydroxybenzoyl)benzofuran was converted to the corresponding (2,3-epoxy)propoxybenzoylbenzofuran which was ring opened with isopropylamine as described in the procedure of Example 7 to give the title compound. The hydrochloric acid salt was formed as described in Example 1, m.p. 151°-153° (ethanol-ether).

EXAMPLE 13

2-n-Butyl-3-[2'-chloro-4'-(2-hydroxy-3-isopropylamino)propoxybenzoyl]benzofuran

2-Chloro-4-methoxybenzoic acid (6.2 g., 0.033 mol.) was converted to the corresponding acid chloride by heating with 75 ml. of thionyl chloride for two hours on a steam bath.

2-n-Butylbezofuran (5.7 g., 0.033 mol.) was acylated with 6.7 g. (0.033 mol.) of 2-chloro-4-methoxybenzoic acid chloride in the presence of 18 g. (0.07 mol.) of stannic chloride as described in the procedure of Example 10 to give 2-n-butyl-3-(2'-chloro-4'-methoxybenzoyl)benzofuran. The subsequent demethylation, epoxy compound formation and ring opening of the epoxide to give the title compound were carried out as previously described in Examples 9 and 7.

EXAMPLE 14

2-n-Butyl-3-[3'-(2-hydroxy-3-isopropylamino)propoxybenzoyl]benzofuran

Acylation of 9.4 g. (0.054 mol.) of 2-n-butylbenzofuran with 9.9 g. (0.058 mol.) of m-anisoyl chloride according to the procedure described in Example 10 gave 2-n-butyl-3-(3'-methoxybenzoyl)benzofuran.

Demethylation of 2-n-butyl-3-(3'-methoxybenzoyl)benzofuran, followed by treatment of the resulting phenol with epichlorohydrin and subsequent epoxide ring opening with isopropylamine as described in Examples 9 and 7 gave the title compound.

EXAMPLE 15

2-n-Butyl-3-[2'-(2-hydroxy-3-isopropylamino)propoxybenzoyl]benzofuran

Acylation of 9.4 g. (0.054 mol.) of 2-n-butylbenzofuran with 9.9 g. (0.058 mol.) of o-anisoyl chloride according to the procedure described in Example 10 gave 2-n-butyl-3-(2'-methoxybenzoyl)benzofuran which was demethylated with pyridine hydrochloride as previously described to give 2-n-butyl-3-(2'-hydroxybenzoyl)benzofuran.

A mixture of 7.5 g. (0.025 mol.) of 2-n-butyl-3-(2'-hydroxybenzoyl)benzofuran, 25 ml. of epichlorohydrin and 15.0 g. of potassium carbonate in 150 ml. of ethanol was refluxed for three hours. After cooling the reaction mixture was filtered and the filtrate was concentrated in vacuo. The residue was dissolved in water and the aqueous solution was extracted with methylene chloride. The extracts were combined, dried (Na₂SO₄) and concentrated to give an oily residue that was chromatographed on alumina with chloroform as the eluant to give 2-n-butyl-3-[2'-(2,3-epoxy)propoxybenzoyl]benzofuran.

The epoxy compound was heated with isopropylamine as described in the procedure of Example 7 to give the title compound.

EXAMPLE 16

2-n-Butyl-3-[4'-chloro-2'-(2-hydroxy-3-isopropylamino)-propoxybenzoyl]benzofuran Acylation of 13.1 g. (0.075 mol.) of 2-n-butylbenzofuran with 15.4 g. (0.075 mol.) of 4-chloro-2-methoxybenzoic acid chloride, prepared from 4-chloro-2-methoxybenzoic acid and thionyl chloride as previously described, according to the procedure of Example 10 gave 2-n-butyl-3-(4'-chloro-2'-methoxybenzoyl)benzofuran. Demethylation as previously described gave 2-n-butyl-3-(4'-chloro-2'-hydroxybenzoyl)benzofuran.

A mixture of 2-n-butyl-3-(4'-chloro-2'-hydroxybenzoyl)benzofuran, 30 ml. of epichlorohydrin and 15 g. of potassium carbonate in 200 ml. of ethanol was refluxed for 18 hours. The reaction mixture was concentrated, water was added to the residue and the aqueous solution was extracted with methylene chloride. The extracts were washed with water, dried (MgSO₄) and concentrated in vacuo to give 2-n-butyl-3-[4'-chloro-2'-(2,3-epoxy)propoxybenzoyl]benzofuran which was purified by dry column chromatography on alumina with chloroform as eluant.

The epoxy compound was heated with isopropylamine as described in the procedure of Example 7 to give the title compound.

EXAMPLE 17

To a solution of 30 g. (0.102 mol.) of 2-n-butyl-3-(4'-hydroxybenzoyl)benzofuran in 100 ml. of dioxane was added a solution of 4.5 g. (0.11 mol.) of sodium hydroxide in 10 ml. of water followed by 50 g. (0.552 mol.) of 3-chloro-2-methylpropene. The mixture was refluxed for 12 hours, then cooled and poured into 450 ml. of water. The aqueous mixture was extracted with ether and the extracts were combined, dried (MgSO₄) and concentrated in vacuo to give 2-n-butyl-3-[4'-(2-methylprop-3-ene)oxybenzoyl]benzofuran which was purified by chromatography on alumina with chloroform as eluant.

To a cooled (ice bath), stirred solution of 10.4 g. (0.03 mol.) of the benzofuran olefin in 25 ml. of methylene chloride was added dropwise a solution of 7.52 g. (0.04 mol.) of m-chloroperbenzoic acid in 100 ml. of methylene chloride. The reaction mixture was allowed to warm to ambient temperature, then it was stirred for one hour. An aqueous solution of sodium sulfite was added to quench the reaction, the layers were separated and the organic layer was washed with 5% aqueous sodium bicarbonate, dried (MgSO₄) and concentrated in vacuo to yield 2-n-butyl-3-[4'-(2-methyl-2,3-epoxy)propoxybenzoyl]benzofuran.

The epoxy compound was heated with isopropylamine in ethanol as described in the procedure of Example 1 to give 2-n-butyl-3-[4'-(2-hydroxy-2-methyl-3-isopropylamino)propoxybenzoyl]benzofuran.

By similar methods, substitution of an equivalent amount of 3-chloro-1-methylpropene in the above procedure followed by the synthetic steps of epoxidation and ring opening of the resultant epoxy compound with isopropylamine gives, ultimately, a mixture of 2-n-butyl-3-[4'-(2-hydroxy-1-methyl-3-isopropylamino) propoxybenzoyl]benzofuran and 2-n-butyl-3-[4'-(2-hydroxy-3-methyl-3-isopropylamino)propoxybenzoyl]benzofuran, which is separated by dry column chromatography on alumina.

EXAMPLE 18

2-[4'-(2-Hydroxy-3-isopropylamino)propoxybenzoyl]-benzofuran

2-[4'-(2,3-epoxy)propoxybenzoyl]benzofuran was prepared from 12.0 g. (0.050 mol.) of 2-(4'-hydroxybenzoyl)benzofuran, 3.0 g. of sodium hydroxide and 30 ml. of epichlorohydrin as described in the procedure of Example 7.

The epoxide ring was opened by heating with isopropylamine as described in Example 7 to give the title compound, m.p. 120°. Preparation of the hydrochloric acid salt was accomplished as described in Example 1, m.p. 158°–160° (ethanol-ether).

EXAMPLE 19

2-[3'-Chloro-4'-(2-hydroxy-3-isopropylamino)propoxybenzoyl]benzofuran

2-[3'-Chloro-4'-(2,3-epoxy)propoxybenzoyl]benzofuran was prepared from 2-(3'-chloro-4'-hydroxybenzoyl)benzofuran and epichlorohydrin according to the procedure described in Example 7.

The epoxide was opened by heating with isopropylamine as described in Example 7 to give the title compound, m.p. 117°–119° (benzene-hexane).

EXAMPLE 20

3-[4'-(2-Hydroxy-3-isopropylamino)propoxybenzoyl]-benzofuran

To a solution of the Grignard reagent prepared from 4.27 g. (0.14 g.-atom) of magnesium turnings and 31.0 g. (0.13 mol.) of 4-iodoanisole in 50 ml. of ether was added dropwise a solution of 10.0 g. (0.07 mol.) of 3-cyanobenzofuran in 150 ml. of ether. The reaction mixture was stirred at 25° for 17 hours, then 30 ml. of water was added followed by a mixture of 20 ml. of sulfuric acid and 40 ml. of water. Additional amounts of the acid solution were added to dissolve the precipitate that formed in the reaction mixture. The mixture was poured into 500 ml. of water and the aqueous solution was extracted with chloroform. The extracts were dried (MgSO₄) and concentrated in vacuo to give 3-(4'-methoxybenzoyl)benzofuran which was purified by chromatography on alumina with chloroform, m.p. 89°–90° (hexane-benzene).

Demethylation with pyridine hydrochloride gave 3-(4'-hydroxybenzoyl)benzofuran which was reacted with epichlorohydrin as previously described in Example 7. The epoxide ring was opened with isopropylamine as described above to give the title compound which was purified by dry column chormatography on alumina with chloroform. The oxalic acid salt was prepared by the procedure of Example 11, m.p. 198°–200° (ethanol).

EXAMPLE 21

2-Methyl-3-[4'-(2-hydroxy-3-isopropylamino)propoxybenzoyl]benzofuran

2-Methylbenzofuran (7.25 g., 0.055 mol.) was acylated with 15.7 g. (0.092 mol.) of anisoyl chloride according to the procedure described in Example 10 to give 2-methyl-3-(4'-methoxybenzoyl)benzofuran.

Demethylation, reaction of the 2-methyl-3-(4'-hydroxybenzoyl)benzofuran with epichlorohydrin and subsequent epoxide ring opening with isopropylamine were accomplished as described in the procedures of Examples 9 and 7 to give the title compound which was purified by dry column chromatography on alumina with chloroform as eluant.

EXAMPLE 22

2-Ethyl-3-(4'-hydroxybenzoyl)benzofuran was treated with epichlorohydrin according to the procedure of Example 7 to give 2-ethyl-3-[4'-(2,3-epoxy)-propoxybenzoyl]benzofuran which was subsequently heated with isopropylamine as previously described to give 2-ethyl-3-[4'-(2-hydroxy-3-isopropylamino)-propoxybenzoyl]benzofuran. The propanolamine was converted to the corresponding hydrochloric acid salt as described in Example 1, m.p. 82°–84° (ether-ethanol).

Similarly, 2-propyl-3-[4'-(2-hydroxy-3-isopropylamino)propoxybenzoyl]benzofuran was prepared by treatment of 2-propyl-3-(4'-hydroxybenzoyl)-benzofuran with epichlorohydrin followed by opening of the epoxide function with isopropylamine as described in the procedure of Example 7.

EXAMPLE 23

2-Phenylbenzofuran (7.81 g., 0.040 mol.) was acylated with 7.0 g. (0.041 mol.) of anisoyl chloride according to the procedure described in Example 10 to give 2-phenyl-3-(4'-methoxybenzoyl)benzofuran.

Demethylation, reaction of the 2-phenyl-3-(4'-hydroxybenzoyl)benzofuran with epichlorohydrin and subsequent epoxide ring opening with isopropylamine were accomplished as described in Examples 9 and 7 to give 2-phenyl-3-[4'-(2-hydroxy-3-isopropylamino)-propoxybenzoyl]benzofuran, m.p. 43°–50°.

In like manner, 2-phenyl-3-[3'-chloro-4'-(2-hydroxy-3-isopropylamino)propoxybenzoyl]benzofuran was prepared by acylation of 2-phenylbenzofuran with 3-chloro-4-methoxybenzoic acid chloride followed by the synthetic sequence of demethylation, reaction with epichlorohydrin and treatment of the 2-phenyl-3-[3'-chloro-4'-(2,3-epoxy)propoxybenzoyl]benzofuran formed with isopropylamine as previously described.

EXAMPLE 24

2-Benzyl-3-[4'-(2-hydroxy-3-isopropylamino)propoxybenzoyl]benzofuran

Acylation of 20.1 g. (0.096 mol.) of 2-benzylbenzofuran with 17.5 g. (0.103 mol.) of anisoyl chloride according to the procedure of Example 10 gave 2-benzyl-3-(4 -methoxybenzoyl)benzofuran which was demethylated with pyridine hydrochloride to give 2-benzyl-3-(4'-hydroxybenzoyl)bezofuran, m.p. 146°–149°.

Subsequent treatment of 2-benzyl-3-(4'-hydroxybenzoyl)benzofuran with epichlorohydrin and ring opening of the epoxide thus formed with isopropylamine as previously described gave the title compound, m.p. 116°–119° (ethanol).

EXAMPLE 25

2-n-Butyl-3-[4'-(2-hydroxy-3-benzylamino)propoxybenzoyl]benzofuran

A mixture of 4.4 g. (0.015 mol.) of 2-n-butyl-3-(4'-hydroxybenzoyl)benzofuran, 4.66 g. (0.034 mol.) of epibromohydrin and 2.08 g. (0.015 mol.) of anhydrous potassium carbonate in 50 ml. of dry acetone was refluxed for 12 hours. The reaction mixture was cooled, filtered and the filtrate was concentrated in vacuo and distilled at reduced pressures to remove all traces of epibromohydrin from the product 2-n-butyl-3-[4'-(2,3-epoxy)propoxybenzoyl]benzofuran.

A solution of 5.14 g. (0.014 mol.) of 2-n-butyl-3-[4'-(2,3-epoxy)propoxybenzoyl]benzofuran and 2.14 g. (0.02 mol.) of benzylamine in 60 ml. of ethanol was refluxed for four hours. Concentration in vacuo gave the title compound which was converted to the corresponding hydrochloric acid salt as described in the procedure of Example 1, m.p. 168°-170°.

EXAMPLE 26

2-(4'-Chlorobenzyl)-3-[4'-(2-hydroxy-3-isopropylamino)propoxybenzoyl]benzofuran

To a solution of 15.3 g. (0.125 mol.) of salicylaldehyde in 100 ml. of acetone was added 7.0 g. (0.125 mol.) of potassium hydroxide dissolved in a minimum amount of water. α-Bromo-p-chloroacetophenone (29.16 g., 0.125 mol.) was added dropwise with stirring and cooling (ice bath). After addition, the reaction mixture was stirred at 25° for 12 hours. The precipitate was collected by filtration, washed with water and combined with the residue remaining after concentration of the filtrate to give 2-(4'-chlorobenzoyl)-3-hydroxycoumaran which was immediately dehydrated in the presence of p-toluenesulfonic acid to yield 2-(4'-chlorobenzoyl)benzofuran.

Hydrazine hydrate (28.0 g., 0.5 mol.) was added to a solution of 42.0 g. (0.16 mol.) of 2-(4'-chlorobenzoyl)-benzofuran in 400 ml. of ethanol and the reaction mixture was refluxed overnight. The solution was concentrated in vacuo, chloroform was added and the chloroform solution was washed with saturated aqueous sodium chloride, dried (MgSO$_4$) and concentrated to yield the corresponding hydrazone. The hydrazone was dissolved in 100 ml. of dry dimethyl sulfoxide and added dropwise over a four hour interval to a slurry of 36.4 g. (0.32 mol.) of potassium t-butoxide in 100 ml. of dry dimethyl sulfoxide. The reaction mixture was poured into 500 ml. of water and the aqueous solution was extracted with chloroform. The extracts were washed with water, dried (MgSO$_4$) and concentrated in vacuo to give 2-(4'-chlorobenzyl)benzofuran which was purified by chromatography on silica gel with carbon tetrachloride as eluant.

Acylation of 2-(chlorobenzyl)benzofuran with anisoyl chloride was accomplished as described in Example 10. Demethylation with pyridine hydrochloride as previously described followed by treatment of the 2-(4'-chlorobenzyl)-3-(4'-hydroxybenzoyl)benzofuran with epibromohydrin as described in the procedure of Example 25 and subsequent epoxide ring opening with isopropylamine according to the procedure of Example 7 gave the title compound. The corresponding hydrochloric acid salt was prepared as described in Example 1, m.p. 115°-119°.

EXAMPLE 27

2-(3'-Trifluoromethylbenzyl)-3-[4'-(2-hydroxy-3-isopropylamino)propoxybenzoyl]benzofuran To a solution of 24.8 g. (0.127 mol.) of m-trifluoromethylacetophenone in 20 ml. of anhydrous ether was added with cooling and stirring 0.15 g. of anhydrous aluminum chloride and 20.2 g. (0.127 mol.) of bromine. The reaction mixture was concentrated in vacuo and the residue was distilled to give α-bromo-m-trifluoromethylacetophenone, b.p. 135°-140° (20mm.).

Substitution of an equivalent amount of α-bromo-m-trifluoromethylacetophenone in the procedure of Example 26 for α-bromo-p-chloroacetophenone followed by treatment of the 2-(3'-trifluoromethylbenzoyl)benzofuran with hydrazine hydrate ultimately gave 2-(3'-trifluoromethylbenzyl)benzofuran, b.p. 195°-197° (25 mm.).

Acylation of 2-(3'-trifluoromethylbenzyl)benzofuran with anisoyl chloride was carried out as outlined in the procedure of Example 10. Demethylation with pyridine hydrochloride, treatment with epichlorohydrin and subsequent epoxide ring opening with isopropylamine were accomplished as described in the procedures of Examples 9 and 7 to give the title compound.

EXAMPLE 28

When 2-(4'-chlorophenyl)benzofuran was acylated with anisoyl chloride as described in the procedure of Example 10 and the resulting 2-(4'-chlorophenyl)-3-(4'-methoxybenzoyl)benzofuran was demethylated with pyridine hydrochloride as previously described, 2-(4'-chlorophenyl)-3-(4'-hydroxybenzoyl)benzofuran was obtained.

Reaction of 2-(4'-chlorophenyl)-3-(4'-hydroxy-benzoyl)benzofuran with epichlorohydrin and subsequent ring opening with isopropylamine according to the procedure of Example 7 gave 2-(4'-chlorophenyl)-3-[4'-(2-hydroxy-3-isopropylamino)propoxybenzoyl]-benzofuran.

Similarly, acylation of 2-(4'-tolyl)benzofuran with anisoyl chloride and subsequent demethylation with pyridine hydrochloride gave 2-(4'-tolyl)-3-(4'-hydroxybenzoyl)benzofuran.

Treatment of 2-(4'-tolyl)-3-(4'-hydroxybenzoyl)benzofuran with epichlorohydrin followed by ring opening of the epoxy compound with isopropylamine as described in the procedure of Example 7 gave 2-(4'-tolyl)-3-[4'-(2-hydroxy-3-isopropylamino)propoxybenzoyl]benzofuran which was converted to the corresponding hydrochloric acid salt as described in Example 1, m.p. 80°-87°.

In like manner, 5-bromo-2(p-bromophenyl)benzofuran is acylated with anisoyl chloride and the resulting 5-bromo-2-(4'-bromophenyl)-3-(4'-methoxybenzoyl)-benzofuran is demethylated and the product treated with epichlorohydrin to give an epoxy compound which is subsequently opened with isopropylamine to give 5-bromo-2-(4'-bromophenyl)-3-[4'-(2-hydroxy-3-isopropylamino)propoxybenzoyl]benzofuran.

EXAMPLE 29

2-n-Butyl-5-chloro-3-[4'-(2-hydroxy-3-isopropylamino)propoxybenzoyl]benzofuran MgSO A mixture of 27 g. (0.18 mol.) of 5-chlorobenzofuran, 28.5 g. (0.18 mol.) of butyric anhydride, 18 g. (0.20 mol.) of butyric acid and 5 g. (0.05 mol.) of phosphoric acid wasa refluxed for four hours then stirred at 25° for 12 hours. The reaction mixture was made basic with 10% aqueous sodium hydroxide, chloroform was added to the mixture and the layers were separated. The organic phase was washed with water, dried MgSO$_4$) and concentrated in vacuo to give 2-butyryl-5-chlorobenzofuran.

A mixture of 31.5 g. (0.14 mol.) of 2-butyryl-5-chlorobenzofuran and 35 ml. of 98% hydrazine in 70 ml. of diethylene glycol was warmed for a few minutes on a steam bath. Then 23.3 g. of potassium hydroxide was added and the reaction mixture was refluxed for two hours. After cooling, water was added to the mixture and the resulting aqueous solution was extracted with benzene. The extract was washed with water, 10% aqueous hydrochloric acid and water, dried (MgSO$_4$) and concentrated in vacuo to yield 2-n-butyl-5-chlorobenzofuran, b.p. 70°–75° (10–15 mm.).

2-n-Butyl-5-chlorobenzofuran (9.5 g., 0.046 mol.) was acylated with 8 g. (0.047 mol.) of anisoyl chloride as described in the procedure of Example 10 to give 2-n-butyl-5-chloro-3-(4'-methoxybenzoyl)benzofuran. Demethylation followed by reaction of the 2-n-butyl-5-chloro-3-(4'-hydroxybenzoyl)benzofuran with epichlorohydrin and subsequent opening of the epoxy compound formed with isopropylamine was carried out as described in the procedures of Examples 9 and 7 to give the title compound.

EXAMPLE 30

5-Chloro-2-phenyl-3-[4'-(2-hydrdoxy-3-isopropylamino)propoxybenzoyl]benzofuran

A mixture of 14.2 g. (0.09 mol.) of cuprous phenylacetylide and 16.0 g. (0.08 mol.) of 2-bromo-4-chlorophenol in 130 ml. of pyridine was refluxed under a nitrogen atmosphere for 18 hours. The reaction mixture was cooled and poured into 600 ml. of water. The resulting precipitate was collected by filtration, washed with copious amounts of water and continuously extracted with ethanol for 12 hours. Removal of the ethanol in vacuo gave a residue which was chromatographed on an alumina dry column with hexane to give 5-chloro-2-phenylbenzofuran, m.p. 140°–143° (methanol).

Acylation of 5-chloro-2-phenylbenzofuran with anisoyl chloride was accomplished as described in the procedure of Example 10 to give 5-chloro-2-phenyl-3-(4'-methoxybenzoyl)benzofuran which was then demethylated and the product treated with epichlorohydrin as described above. Opening of the epoxide ring with isopropylamine as previously described gave the title compound.

EXAMPLE 31

A solution of 7.0 g. (0.017 mol.) of 2-n-butyl-3-[4'-(2-hydroxy-3-isopropylamino)propoxybenzoyl]benzofuran in 60 ml. of acetic anhydride was refluxed for six hours. The cooled reaction mixture was poured into ice water and the aqueous solution was extracted with chloroform. The extracts were washed with 5% aqueous sodium bicarbonate and water, dried (MgSO$_4$) and concentrated in vacuo to give a mixture of 2-n-butyl-3-[4'-(2-acetoxy-3-N-acetylisopropylamino)-propoxybenzoyl]benzofuran, 2-n-butyl-3-[4'-(2-acetoxy-3-isopropylamino)propoxybenzoyl]benzofuran and 2-n-butyl-3-[4'-(2-hydroxy-3-N-acetylisopropylamino)-propoxybenzoyl]-benzofuran which was separated by dry column chromatography on alumina with chloroform as eluant.

Alternatively, 2-n-butyl-3-[4'-(2-hydroxy-3-N-acetylisopropylamino)propoxybenzoyl]benzofuran was prepared by refluxing 4.9 g. (0.01 mol.) of 2-n-butyl-3-[4'-(2-acetoxy-3-N-acetylisopropylamino)-propoxybenzoyl]benzofuran with 5 ml. of 10% aqueous sodium hydroxide in 20 ml. of water for 1 hour. After cooling, chloroform was added to the reaction mixture, the layers were separated and the organic phase was washed with water, dried (Na$_2$SO$_4$) and concentrated in vacuo to give the desired product.

In like manner, the (2-acetoxy-3-N-acetylamino)-, (2-acetoxy-3-alkylamino)- and (2-hydroxy-3-N-acetylamino)-derivatives of the other (2-hydroxy-3-alkylamino)- benzofurans disclosed herein may be obtained.

EXAMPLE 32

By the procedure of Example 31, using propionic anhydride in place of acetic anhydride, the products are 2-n-butyl-3-[4'-(2-propionyloxy-3-N-propionylisopropylamino)-propoxybenzoyl]benzofuran, 2-n-butyl-3-[4'-(2-propionyloxy-3-isopropylamino)-propoxybenzoyl]benzofuran and 2-n-butyl-3-[4'-(2-hydroxy-3-N-propionylisopropylamino)propoxybenzoyl]benzofuran.

Similarly, using n-butyric anhydride, the products are 2-n-butyl-3-[4'-(2-n-butyryloxy-3-N-n-butyrylisopropyl-amino)propoxybenzoyl]benzofuran, 2-n-butyl-3-[4'-(2-n-butyryloxy-3-isopropylamino)propoxybenzoyl]benzofuran and 2-n-butyl-3-[4'-(2-hydroxy-3-N-n-butyrylisopropylamino)-propoxybenzoyl]benzofuran.

In like manner, the (2-propionyloxy-3-N-propionylamino)-, (2-propionyloxy-3-alkylamino)-, (2-hydroxy-3-N-propionylamino)-, (2-n-butyryloxy-3-N-n-butyrylamino)-, (2-n-butyryloxy-3-alkylamino)- and (2-hydroxy-3-N-n-butyrylamino) derivatives of the other (2-hydroxy-3-alkylamino)- benzofurans disclosed herein may be obtained.

EXAMPLE 33

2-n-Butyl-3-[4'-(2-acetoxy-3-piperidino)propoxybenzoyl]-benzofuran

Substitution of an equivalent amount of 2-n-butyl-3-[4'-(2-hydroxy-3-piperidino)propoxybenzoyl]benzofuran in the procedure of Example 31 for 2-n-butyl-3-[4'-(2-hydroxy-3-isopropylamino)propoxybenzoyl]benzofuran gives the title compound.

Likewise, substitution of the other (2-hydroxy-3-dialkylamino)-, (2-hydroxy-3-pyrrolidino)- or (2-hydroxy-3-morpholino)- benzofurans disclosed above gives the corresponding (2-acetoxy-3-substitutedamino)-benzofurans.

EXAMPLE 34

Substitution of the following benzofurans:
3-(3', 5'-dibromo-4'-hydroxybenzoyl)-2-ethylbenzofuran
3-ethyl-2-(4'-hydroxybenzoyl)benzofuran
2-(3'-chloro-4'-hydroxybenzoyl)benzofuran
2-(3'-fluoro-4'-hydroxybenzoyl)benzofuran
2-(2'-hydroxy-5'-methylbenzoyl)benzofuran
3-(3',5'-diiodo-4'-hydroxybenzoyl)-2-ethylbenzofuran 2-(2'-hydroxybenzoyl)benzofuran in the procedure of Example 7 for 2-n-butyl-3-(4'-hydroxy-benzoyl)benzofuran with subsequent opening of the intermediate epoxy compound with isopropylamine as described in Example 7 gives, respectively:
3-[3',5'-dibromo-4'-(2-hydroxy-3-isopropylamino)-propoxybenzoyl]-2-ethylbenzofuran
3-ethyl-2-[4'-(2-hydroxy-3-isopropylamino)-propoxy-benzoyl]benzofuran
2-[3'-chloro-4'-(2-hydroxy-3-isopropylamino)-propoxy-benzoyl]benzofuran
2-[3'-fluoro-4'-(2-hydroxy-3-isopropylamino)-propoxy-benzoyl]benzofuran 2-[5'-methyl-2'-(2-hydroxy-3-isopropylamino)-propoxy-benzoyl]benzofuran 3-[3',5'-diiodo-4'-(2-hydroxy-3-isopropylamino)-propoxybenzoyl]-2-ethylbenzofuran 2-[2'-(2-hydroxy-3-isopropylamino)propoxybenzoyl]-benzofuran.

EXAMPLE 35

Substitution of an equivalent amount of 2-(chloromethyl)butene in the procedure of Example 17 for 3-chloro-2-methylpropene followed by treatment of the product with m-chloroperbenzoic acid and subsequent opening of the epoxy compound formed with isopropylamine as described in Examples 17 and 7 gives 2-n-butyl-3-[4'-(2-ethyl-2-hydroxy-3-isopropylamino)propoxybenzoyl]benzofuran.

In like manner, when an equivalent amount of 3-chloro-1-pentene is substituted in the procedure of Example 17 for 3-chloro-2-methylpropene and the product is treated with m-chloroperbenzoic acid and subsequently heated with isopropylamine as described above, there is prepared a mixture of 2-n-butyl-3-[4'-(1-ethyl-2-hydroxy-3-isopropylamino)propoxy-benzoyl]benzofuran and 2-n-butyl-3-[4'-(3-ethyl-2-hydroxy-3-isopropylamino)propoxybenzoyl]benzofuran which is separated by chromatography on alumina.

EXAMPLE 36

When an equivalent amount of diethyl amine is substituted in the procedure of Examples 1 or 3 for isopropylamine or piperidine, 2-n-butyl-3-[4'-(2-hydroxy-3-diethylamino)propoxybenzoyl]benzofuran is obtained.

In a similar manner, reaction of 2-n-butyl-3-[4'-(2,3-epoxy)propoxybenzoyl]benzofuran with di-n-butylamine gives 2-n-butyl-3-[4'-(2-hydroxy-3-di-n-butylamino)propoxy-benzoyl]benzofuran.

Likewise, substitution of N-ethyl-N-methylamine in the procedure of Example 1 or Example 3 for isopropylamine or piperidine gives 2-n-butyl-3-[4'-(2-hydroxy-3-N-ethyl-N-methylamino)propoxybenzoyl]-benzofuran.

EXAMPLE 37

Substitution of an equivalent amount of a benzofuran listed below:
5-bromobenzofuran
6-chlorobenzofuran
7-chlorobenzofuran
4-methylbenzofuran
5-methylbenzofuran
5-ethylbenzofuran in the procedure of Example 29 for 5-chlorobenzofuran followed by the synthetic steps of hydrazine reduction, acylation, demethylation, epoxide formation and opening of the epoxide with isopropylamine as described therein gives, ultimately, the following substituted benzofurans:

5-bromo-2-n-butyl-3-[4'-(2-hydroxy-3-isopropylamino)-propoxybenzoyl]benzofuran 2-n-butyl-6-chloro-3-[4'-(2-hydroxy-3-isopropylamino)propoxybenzoyl]benzofuran 2-n-butyl-7-chloro-3-[4'-(2-hydroxy-3-isopropylamino)propoxybenzoyl]benzofuran 2-n-butyl-3-[4'-(2-hydroxy-3-isopropylamino)-propoxybenzoyl]-4-methylbenzofuran 2-n-butyl-3-[4'-(2-hydroxy-3-isopropylamino)-propoxybenzoyl]-5-methylbenzofuran 2-n-butyl-5-ethyl-3-[4'-(2-hydroxy-3-isopropylamino)-propoxybenzoyl]benzofuran

EXAMPLE 38

When an equivalent amount of 5-chloro-2-ethylbenzofuran is substituted in the procedure of Example 10 for 2-n-butylbenzofuran and the product is demethylated with pyridine hydrochloride, followed by treatment of the hydroxyphenyl benzofuranyl ketone with epichlorohydrin and subsequent ring opening of the resulting epoxy compound with isopropylamine as previously described, there is obtained 5-chloro-2-ethyl-3-[4'-(2-hydroxy-3-isopropylamino)propoxybenzoyl]-benzofuran.

In like manner, 3-[4'-(2-hydroxy-3-isopropylamino)-propoxybenzoyl]-2-phenyl-7-trifluoromethylbenzofuran is obtained from substitution of an equivalent amount of 2-phenyl-7-trifluoromethylbenzofuran in the procedure of Example 10 for 2-n-butylbenzofuran followed by the subsequent synthetic steps of demethylation, treatment with epichlorohydrin and heating the epoxy compound thus formed with isopropylamine.

EXAMPLE 39

2-n-Butyl-3-[3'-methoxy-4'-(2-hydroxy-3-isopropylamino)-propoxybenzoyl]benzofuran A mixture of 17.4 g. (0.1 mol.) of 2-n-butyl-benzofuran and 19.1 g. (0.1 mol.) of 4-acetoxy-3-methoxy-benzonitrile in 20 ml. of trifluoroacetic acid is refluxed for three hours. The reaction mixture is cooled, diluted with 200 ml. of water and the resulting aqueous solution is extracted with ether. The extracts are concentrated to dryness and the residue is dissolved in 100 ml. of ethanol and heated with 20 ml. of 10% aqueous sodium carbonate for two hours. The mixture is concentrated, the residue extracted with ether and the extracts are dried and concentrated in vacuo to give 2-n-butyl-3-(3'-methoxy-4'-hydroxybenzoyl)-benzofuran.

2-n-Butyl-3-(3'-methoxy-4'-hydroxybenzoyl)benzofuran is reacted with epichlorohydrin and the resultant epoxy compound is heated with isopropylamine as previously described to give the title compound.

EXAMPLE 40

2-(4'-Aminobenzyl)-3-[4'-(2-hydroxy-3-isopropylamino)-propoxybenzoyl]benzofuran

Substitution of an equivalent amount of α-bromo-p-nitroacetophenone in the procedure of Example 26 for α-bromo-p-chloroacetophenone gives 2-(4'-nitrobenzoyl)benzofuran.

Sodium borohydride (7.4 g., 0.2 mol.) is added portionwise to a rapidly stirred solution of 26.7 g. (0.1 mol.) of 2-(4'-nitrobenzoyl)benzofuran in methanol. The reaction mixture stirred at 25° for one hour then quenched by addition of water. The aqueous slurry is extracted with chloroform, the extracts are dried (MgSO$_4$) and the solvent is removed in vacuo to give 2-(α-hydroxy-4'-nitrobenzyl)benzofuran which is immediately converted to the corresponding α-chloride by reaction with 14.3 g. (0.12 mol.) of thionyl chloride.

A mixture of 13.6 g. (0.36 mol.) of sodium borohydride and 14.4 g. (0.05 mol.) of 2-(α-chloro-4'-nitrobenzyl)benzofuran in 200 ml. of 80% aqueous diglyme is stirred at 50° for four hours. The reaction mixture is then cooled and hexane followed by 4.0 g. (0.1 mol.) of sodium hydroxide are added. The layers are separated and the organic phase is dried (MgSO$_4$) and concentrated to give 2-(4'-nitrobenzyl)benzofuran.

2-(4'-Nitrobenzyl)benzofuran is acylated with anisoyl chloride as described in Example 10. Demethylation with pyridine hydrochloride as previously described gives 3-(4'-hydroxybenzoyl)-2-(4'-nitrobenzyl)benzofuran.

3-(4'-Hydroxybenzoyl)-2-(4'-nitrobenzyl)benzofuran (37.3 g., 0.1 mol.) is added in small portions to 56.4 g. (0.25 mol.) of stannous chloride dihydrate in 70 ml. of concentrated hydrochloric acid. The reaction mixture is heated at 50° for 3 hours, then stirred at 25° for 12 hours. Cooling (ice bath) enhances precipitation of the product salt which is collected by filtration and dissolved in water. The aqueous solution is made basic by addition of 10% aqueous sodium hydroxide and extracted with chloroform. The extracts are dried ($MgSO_4$) and concentrated to give 2-(4'-aminobenzyl)-3-(4'-hydroxybenzoyl)benzofuran.

Reaction of 2-(4'-aminobenzyl)-3-(4'-hydroxy-benzoyl)benzofuran with epichlorohydrin followed by subsequent opening of the epoxy compound thus formed with isopropylamine as previously described gives the title compound.

EXAMPLE 41

2-(4'-N,N-Dimethylaminobenzyl)-3-[4'isopropylamine
2-hydroxy-3-isopropylamino)propoxybenzoyl]benzofuran A mixture of 2-(4'-aminobenzyl)-3-(4'-hydroxy-benzoyl)benzofuran (34.3 g., 0.1 mol.), 35.5 g. (0.25 mol.) of methyl iodide and 31.8 g. (0.3 mol.) of sodium carbonate in 250 ml. of water is refluxed for three hours then cooled to 25° and extracted with chloroform. The extracts are dried ($MgSO_4$) and concentrated in vacuo to give 2-(4'-N,N-dimethylaminobenzyl)-3-(4'-hydroxybenzoyl)benzofuran.

Treatment of 2-(4'-N,N-dimethylaminobenzyl)-3-(4'-hydroxybenzoyl)benzofuran with epichlorohydrin with subsequent opening of the epoxy compound thus formed with isopropylamine by methods outlined above gives the title compound.

EXAMPLE 42

2-(3'-Anilino)-3-[4'-(2-hydroxy-3-isopropylamino)-propoxybenzoyl]benzofuran

A solution of 20 g. (0.105 mol.) of cuprous iodide in 400 ml. of ammonium hydroxide is poured with stirring into a solution of 15.4 g. (0.105 mol.) of m-nitrophenylacetylene in 500 ml. of ethanol. The reaction mixture is left to stand at 25° for 30 minutes then it is filtered and the product washed five times each with water, ethanol and ether to give cuprous m-nitrophenylacetylide.

A mixture of 5.3 g. (0.024 mol.) of o-iodophenol and 5.0 g. (0.024 mol.) of cuprous m-nitrophenylacetylide in 100 ml. of pyridine is refluxed for 7 hours under a nitrogen atmosphere. The reaction mixture is poured into water, the aqueous slurry filtered and the filtrate is extracted with methylene chloride. The extracts are washed with water, dried ($MgSO_4$) and concentrated to give 2-m-nitrophenylbenzofuran.

Acylation of 2-m-nitrophenylbenzofuran with anisoyl chloride is accomplished as described in the procedure of Example 10. Demethylation with pyridine hydrochloride as previously described gives 3-(4'-hydroxybenzoyl)- 2-(3'-nitrophenyl)benzofuran.

2-(3'-Aminophenyl)-3-(4'-hydroxybenzoyl)benzofuran is prepared by reduction of 3-(4'-hydroxybenzoyl)-2-(3'-nitrophenyl)benzofuran according to the procedure of Example 40. Reaction of this compound with epichlorohydrin followed by ring opening of the resultant epoxy compound with isopropylamine as previously described gives the title compound.

EXAMPLE 43

2-(3'-N-Ethylanilino)-3-[4'-(2-hydroxy-3-isopropylamino)-propoxybenzoyl]benzofuran Substitution of 32.9 g. (0.1 mol.) of 2-(3'-anilino)-3-(4'-hydroxybenzoyl)benzofuran and 15.6 g. (0.1 mol.) of ethyl iodide in the procedure of Example 41 for 2-(4'-aminobenzyl)-3-(4'-hydroxybenzoyl)benzofuran and methyl iodide, respectively, gives 2-(3'-N-ethylanilino)-3-(4'-hydroxybenzoyl)benzofuran.

Treatment of 2-(3'-N-ethylanilino)-3-(4'-hydroxybenzoyl)benzofuran with epichlorohydrin followed by opening of the resultant epoxy compound with isopropylamine according to methods described above gives the title compound.

EXAMPLE 44

When equivalent amounts of o-hydroxyacetophenone or o-hydroxybenzophenone are substituted in the procedure of Example 26 for salicylaldehyde and α-bromo-p-methoxyacetophenone is substituted for α-bromo-p-chloroacetophenone, there are ultimately obtained 3-methyl-2-(4'-methoxybenzoyl)-benzofuran and 3-phenyl-2-(4'-methoxybenzoyl)benzofuran.

Demethylation of 3-methyl-2-(4'-methoxybenzoyl)-benzofuran with pyridine hydrochloride as previously described followed by treatment of the 3-methyl-2-(4'-hydroxybenzoyl)benzofuran with epichlorohydrin and subsequent opening of the intermediate epoxy compound with isopropylamine as described herein gives 2-[4'-(2-hydroxy-3-isopropylamino)propoxybenzoyl]-3-methylbenzofuran.

Similarly, 3-phenyl-2-(4'-methoxybenzoyl)benzofuran is demethylated and the resultant 2-(4'-hydroxybenzoyl)-3-phenylbenzofuran is reacted with epichlorohydrin followed by ring opening of the epoxy compound thus formed with isopropylamine to give 2-[4'-(2-hydroxy-3-isopropylamino)-propoxybenzoyl]-3-phenylbenzofuran.

EXAMPLE 45

Acylation of 5-t-butoxy-2-ethylbenzofuran with anisoyl chloride according to the procedure of Example 10 with subsequent demethylation, reaction with epichlorohydrin and opening of the resulting epoxy compound with isopropylamine gives 5-t-butoxy-2-ethyl-3-[4'-(2-hydroxy-3-isopropylamino)propoxybenzoyl]benzofuran.

Similarly, 2-(p-ethoxybenzyl)benzofuran is acylated and the 2-(4'-ethoxybenzyl)-3-(4'-methoxybenzoyl)-benzofuran is demethylated, the product treated with epichlorohydrin and the resultant epoxy compound opened with isopropylamine to give 2-(4'-ethoxybenzyl)-3-[4'-(2-hydroxy3-isopropylamino)propoxybenzoyl]benzofuran.

EXAMPLE 46

When an equivalent amount of 4-methoxybenzofuran or 5-methoxybenzofuran is substituted in the procedure of Example 29 for 5-chlorobenzofuran there are prepared 2-n-butyl-4-methoxybenzofuran and 2-n-butyl-5-methoxybenzofuran.

Reaction of 2-n-butyl-4- and 5-methoxybenzofuran with 4-acetoxybenzonitrile and hydrolysis of the products with aqueous sodium carbonate as described in the procedure of Example 39, followed by reaction of the 2-n-butyl-3-(4'-hydroxybenzoyl)-4- and 5-methoxybenzofurans thus formed with epichlorohydrin and subsequent epoxide ring opening with isopropylamine as previously described gives, respectively, 2-n-butyl-3-[4'-(2-hydroxy-3-isopropylamino)propoxybenzoyl]4-methoxybenzofuran and 2-n-butyl-3-[4'-(2-hydroxy-3-isopropylamino)propoxybenzoyl]-5-methoxybenzofuran.

EXAMPLE 47

| Ingredients | Amounts |
| --- | --- |
| 2-n-Butyl-3-[4'-(2-hydroxy-3-isopropylamino)propoxybenzoyl]-benzofuran | 100 mg. |
| Calcium sulfate dihydrate | 150 mg. |
| Sucrose | 25 mg. |
| Starch | 15 mg. |
| Talc | 5 mg. |
| Stearic acid | 3 mg. |

The sucrose, calcium sulfate dihydrate and 2-n-butyl3-[4'-(2-hydroxy-3-isopropylamino)propoxybenzoyl]benzofuran are thoroughly mixed and granulated with 10% gelatin solution. The wet granules are screened, dried and then mixed with the starch, talc and stearic acid, screened and compressed into a tablet.

EXAMPLE 48

| Ingredients | Amounts |
| --- | --- |
| 2-(4'-Chlorobenzyl)-3-[4'-(2-hydroxy-3-isopropylamino)propoxybenzoyl]-benzofuran | 150 mg. |
| Magnesium stearate | 5 mg. |
| Lactose | 100 mg. |

The ingredients are mixed and filled into a hard gelatin capsule.

Similarly, the other substituted benzofurans of Formula I or pharmaceutically acceptable acid addition salts thereof may be formulated into tablets and capsules by the procedures of Examples 47 and 48.

The compositions prepared as in Examples 47 and 48 are administered orally to a subject in need of coronary vasodilator activity within the dose ranges given hereabove.

What is claimed is:

1. A pharmaceutical composition having coronary vasodilator activity, in dosage unit form, comprising a pharmaceutical carrier and, in an amount sufficient to produce coronary vasodilation, a substituted benzofuran of the formula:

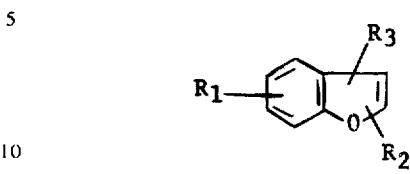

or a pharmaceutically acceptable acid addition salt thereof, in which:

$R_1$ is hydrogen, halogen, lower alkyl, lower alkoxy or trifluoromethyl;

$R_2$ is hydrogen, lower alkyl or phenyl $(CH_2)_n$ where $n$ is 0 or 1 and the phenyl moiety is optionally substituted with lower alkyl, lower alkoxy, trifluoromethyl, halogen, $NH_2$, NH(lower alkyl) or N(lower alkyl)$_2$;

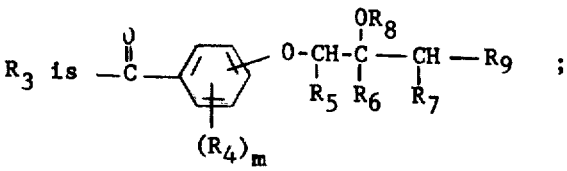

$R_4$ is hydrogen, halogen, lower alkyl or lower alkoxy; $m$ is 1 or 2;

$R_5$, $R_6$ and $R_7$ are hydrogen or one of $R_5$, $R_6$ and $R_7$ is methyl or ethyl;

$R_8$ is hydrogen or lower alkanoyl; and $R_9$ is NH(lower alkyl), N(lower alkyl)$_2$, NH(benzyl), N(lower alkanoyl)(lower alkyl), piperidino, pyrrolidino, morpholino or succinimido.

2. The pharmaceutical composition of claim 1 in which $R_2$ is hydrogen, lower alkyl or phenyl($CH_2$)$_n$ where $n$ is 0 or 1 and the phenyl moiety is optionally substituted with methyl, methoxy, trifluoromethyl or chloro, $R_5$, $R_7$ and $R_8$ are hydrogen, $R_6$ is hydrogen or methyl and $R_9$ is NH(isopropyl) or NH(t-butyl).

3. The pharmaceutical composition of claim 2 in which $R_1$ is hydrogen,

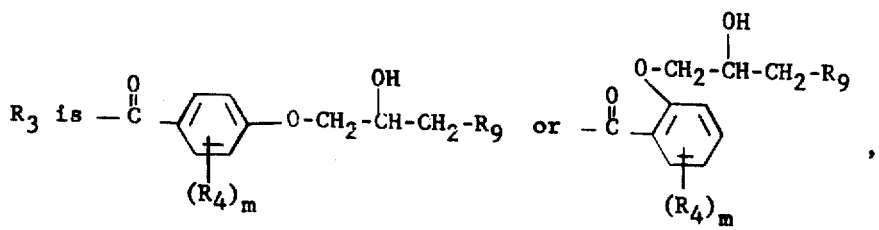

$R_4$ is hydrogen or chloro and m is 1.

4. The pharmaceutical composition of claim 3 in which the substituted benzofuran is 2-n-butyl-3-[4'-(2-hydroxy-3-isopropylamino)propoxybenzoyl]benzofuran.

5. The pharmaceutical composition of claim 3 in which the substituted benzofuran is 2-n-butyl-3-[3'-chloro4'-(2-hydroxy-3-isopropylamino)propoxybenzoyl]benzofuran.

6. The pharmaceutical composition of claim 3 in which the substituted benzofuran is 2-n-butyl-3-[4'- chloro2'-(2-hydroxy-3-isopropylamino)propoxybenzoyl]benzofuran.

7. The pharmaceutical composition of claim 3 in which the substituted benzofuran is 2-(4'-chlorobenzyl)-3-[4'-(2-hydroxy-3-isopropylamino)propoxybenzoyl]benzofuran.

8. The pharmaceutical composition of claim 1 in which the substituted benzofuran is present in an amount of from about 100 mg. to about 600 mg.

9. A method of producing coronary vasodilation which comprises administering internally to an animal, in an amount sufficient to produce coronary vasodilation, a substituted benzofuran of the formula:

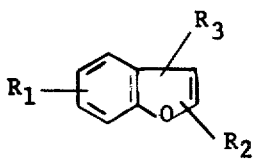

or a pharmaceutically acceptable acid addition salt thereof, in which:

$R_1$ is hydrogen, halogen, lower alkyl, lower alkoxy or trifluoromethyl;

$R_2$ is hydrogen, lower alkyl or phenyl($CH_2$)$_n$ where $n$ is 0 or 1 and the phenyl moiety is optionally substituted with lower alkyl, lower alkoxy, trifluoromethyl, halogen, $NH_2$, NH(lower alkyl) or N(lower alkyl)$_2$;

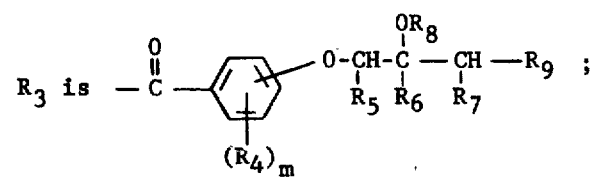

$R_4$ is hydrogen, halogen, lower alkyl or lower alkoxy; $m$ is 1 or 2;

$R_5$, $R_6$ and $R_7$ are hydrogen or one of $R_5$, $R_6$ and $R_7$ is methyl or ethyl;

$R_8$ is hydrogen or lower alkanoyl; and $R_9$ is NH(lower alkyl), N(lower alkyl)$_2$, NH(benzyl), N(lower alkanoyl)(lower alkyl), piperidino, pyrrolidino, morpholino or succinimido.

10. The method of claim 9 in which $R_2$ is hydrogen, lower alkyl or phenyl($CH_2$)$_n$ where n is 0 or 1 and the phenyl moiety is optionally substituted with methyl, methoxy, trifluoro methyl or chloro, $R_5$, $R_7$ and $R_8$ are hydrogen, $R_6$ is hydrogen or methyl and $R_9$ is NH(isopropyl) or NH(t-butyl).

11. The method of claim 10 in which $R_1$ is hydrogen,

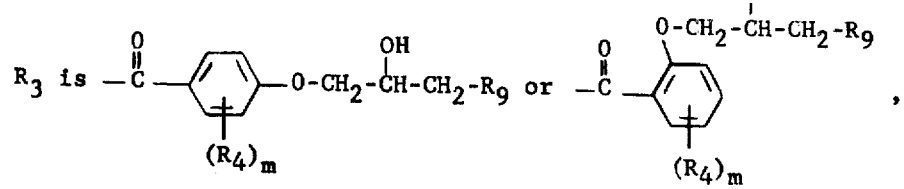

$R_4$ is hydrogen or chloro and $m$ is 1.

12. The method of claim 11 in which the substituted benzofuran is 2-n-butyl-3-[4'-(2-hydroxy-3-isopropylamino)-propoxybenzoyl]benzofuran.

13. The method of claim 11 in which the substituted benzofuran is 2-n-butyl-3-[3'-chloro-4'-(2-hydroxy-3-isopropylamino)propoxybenzoyl]benzofuran.

14. The method of claim 11 in which the substituted benzofuran is 2-n-butyl-3-[4'-chloro-2'-(2-hydroxy-3-isopropylamino)propoxybenzoyl]benzofuran.

15. The method of claim 11 in which the substituted benzofuran is 2-(4'-chlorobenzyl)-3-[4'-(2-hydroxy-3-isopropylamino)propoxybenzoyl]benzofuran.

16. The method of claim 11 in which the substituted benzofuran is administered in a daily dosage of from about 200 mg. to about 1,200 mg.

17. A method of producing anti-anginal activity which comprises administering internally to an animal, in an amount sufficient to produce anti-anginal activity, a substituted benzofuran of the formula;

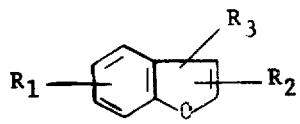

or a pharmaceutically acceptable acid addition salt thereof, in which:

$R_1$ is hydrogen;

$R_2$ is hydrogen, lower alkyl or phenyl($CH_2$)$_n$ where $n$ is 0 or 1 and the phenyl moiety is optionally substituted with lower alkyl, lower alkoxy, trifluoromethyl, halogen, $NH_2$, NH(lower alkyl) or N(lower alkyl)$_2$;

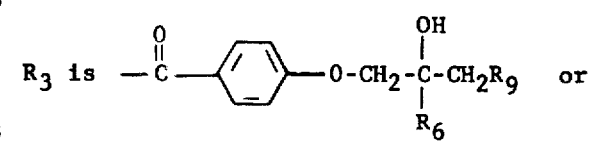

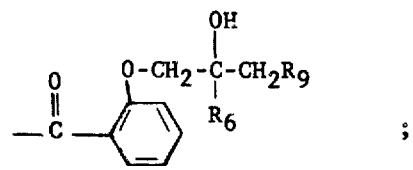

$R_6$ is hydrogen or methyl; and $R_9$ is NH(lower alkyl), N(lower alkyl)$_2$ or NH(benzyl).

* * * * *